United States Patent
Garcia et al.

(10) Patent No.: US 10,753,935 B2
(45) Date of Patent: Aug. 25, 2020

(54) PROGNOSTIC METHOD AND KITS USEFUL IN SAID METHOD

(71) Applicant: Zelda Therapeutics Operations Pty Ltd, Perth (AU)

(72) Inventors: Cristina Sánchez Garcia, Madrid (ES); Sandra Blasco Benito, Madrid (ES); Eduardo Pérez Gómez, Madrid (ES)

(73) Assignee: Zelda Therapeutics Operations Pty Ltd., Perth ( * ) Notice: Subject to any disclaimer, the term of this patent is extended or adjusted under 35 U.S.C. 154(b) by 0 days.

(21) Appl. No.: 16/028,704

(22) Filed: Jul. 6, 2018

(65) Prior Publication Data

US 2018/0313840 A1 Nov. 1, 2018

Related U.S. Application Data

(63) Continuation of application No. PCT/AU2017/051145, filed on Oct. 20, 2017.

(30) Foreign Application Priority Data

Oct. 21, 2016 (AU) ................................ 2016904288

(51) Int. Cl.
*G01N 33/574* (2006.01)
*G01N 33/68* (2006.01)

(52) U.S. Cl.
CPC ... *G01N 33/57415* (2013.01); *G01N 33/6845* (2013.01); *G01N 2333/71* (2013.01)

(58) Field of Classification Search
CPC ......... G01N 33/57415; G01N 2333/71; G01N 2500/02
See application file for complete search history.

(56) References Cited

U.S. PATENT DOCUMENTS 6,630,318 B1 * 10/2003 Margolis .............. C07K 14/475
424/9.1
8,518,405 B2 8/2013 Mukherjee

FOREIGN PATENT DOCUMENTS

| RU | 2595403 | 11/2014 |
| WO | WO 2001/61037 | 8/2001 |
| WO | WO 2013/057487 | 4/2013 |

OTHER PUBLICATIONS

Pérez-Gómez et al., J.Natl. Cancer Inst., Apr. 8, 107(6):djv077, supplemental methods, pp. 1-17 (Year: 2015).*
Ayakannu et al., "The Encocannabinoid System and Sex Steroid Hormone-Dependent Cancers," Int. J Endocrinology, Oct. 2013, 15 pages.
Blasco-Benito et al. [online], "P018 THC as an anti-HER2 therapy in breast cancer," Complutense Universtiy, Madrid, Spain, Sep. 2015, URL < https://www.biochemistry.org/Portals/0/Conferences/Abstracts/SA173/SA173P018.pdf, 1 page.
Caffarel et al., "Cannabinoids reduce ErbB2-driven breast cancer progression through Akt inhibition," Molecular Cancer, Jul. 2010, retrieved on Jan. 10, 2018, URL < https://molecular-cancer.biomedcentral.com/articles/10.1186/1476-4598-9-196>, 20 pages.
Caffarel et al., "Cannabinoids: A new hope for breast cancer therapy?" Cancer Treatment Reviews, Nov. 2012, 38(7): 911-918.
Ladin et al., "Preclinical and Clinical Assessment of Cannabinoids as Anti-Cancer Agents," Frontiers in Pharmacology, Oct. 2016, 7: 361.
PCT International Search Report and Written Opinion in International Appln. No. PCT/AU2017/051146, dated Nov. 27, 2017, 14 pages.
PCT International Preliminary Report on Patentability in International Appln. No. PCT/AU2017/051146, dated May 8, 2018, 7 pages.
Perez-Gomez et al., "Role of Cannabinoid Receptor $CB_2$ in HER2 Pro-oncogenic Signaling in Breast Cancer," J Natl Cancer Inst, Feb. 2015, 107(6): 13 pages.
Soderberg et al., "Characterizing proteins and their interactions in cells and tissues using the in situ proximity ligation assay," Methods, 2008, 45: 227-232.
Trifilieff et al., "Detection of antigen interactions ex vivo by proximity ligation assay: endogenous dopamine D2-adenosine A2A receptor complexes in the striatum," Fish & Richardson P.C. BioTechniques, 2011, 51: 111-118.
Velasco et al., "The use of cannabinoids as anticancer agents," Progress in Neuro-Psychopharmacology & Biological Psychiatry, Jan. 2016, 64: 259-266.
Singapore Written Opinion in Appln. No. 11201805478W, dated Oct. 29, 2018, 14 pages.
Guerrero M. et al., "The chemokine receptor CXCR4 and the cannabinoid receptor CB2R form heterodimers in non-Hodgkin lymphoma (NHL) and solid tumors leading to functional crosstalk", Proceedings: AACR 107th Annual Meeting, Apr. 16, 2016.
RU Office Action in Russian Appln. No. 2018126086/04, dated Feb. 28, 2019, 17 pages (with English translation).

* cited by examiner

*Primary Examiner* — Hong Sang
(74) *Attorney, Agent, or Firm* — Fish & Richardson P.C.

(57) ABSTRACT

The invention generally relates to diagnostic, prognostic, and monitoring methods and assays for breast cancer and kits that may be used in such methods. More particularly, the invention relates to a method of prognosis of a patient afflicted with breast cancer, including determining the level of HER2/$CB_2$ heteromer expression in a biological sample obtained from the patient.

11 Claims, 6 Drawing Sheets

PROGNOSTIC METHOD AND KITS USEFUL IN SAID METHOD

CLAIM OF PRIORITY

This application claims priority to PCT Application No. PCT/AU2017/051146, filed on Oct. 20, 2017, which claims the benefit of Australian Patent Application No. 2016904288, filed on Oct. 21, 2016. The entire contents of the foregoing are hereby incorporated by reference.

FIELD

The invention generally relates to diagnostic, prognostic, and monitoring methods and assays for breast cancer and kits that may be used in such methods.

More particularly, the application relates to the use of HER2/$CB_2$ heteromer expression for predicting the likelihood of the length of local disease-free survival. An assessment of the likelihood of metastasis, length of overall survival of breast cancer patients and the outcome of breast cancer therapies is also possible. It further relates to improved drug targets.

BACKGROUND

Breast cancer is one of the most frequent malignancies worldwide and represents an important public health problem. Despite ongoing improvements in understanding the disease, breast cancer has remained to a large extent resistant to medical intervention. Most clinical initiatives are focused on early diagnosis, followed by conventional forms of intervention, particularly surgery, radiation, hormone suppression, and chemotherapy. Such interventions are of limited success, particularly in patients where the tumour has undergone metastasis. Thus, there is a pressing need to improve the arsenal of diagnostic tools and methods to provide more precise and more effective information that will allow successful treatment in the least invasive way possible. There is also a continuing requirement to identify further and better targets for drug treatment.

In past years, breast cancer has been classified into different subtypes according to molecular parameters. One subtype is characterized by the overexpression of the human epidermal growth factor receptor 2 (HER2), and represents 20%-25% of all breast carcinomas. Separately, it has been demonstrated that $CB_2$ is overexpressed in HER2+ breast cancer, and that $CB_2$ promotes tumor generation and progression by activating HER2 pro-oncogenic signalling via the c-SRC kinase. It has also been shown that $CB_2$ forms heteromers with HER2 in human breast cancer samples.

There is a continuing need to develop better tools for diagnosing, prognosing, and monitoring breast cancer and especially HER2+ breast cancer. It is also important to identify new therapeutic targets.

SUMMARY

It has been discovered by the inventors that the HER2/$CB_2$ expression correlates with local disease-free survival in patients with breast cancer. It was also recently described that HER2/$CB_2$ are present as a heteromer in breast cancer cells. The inventors have also shown that the expression of HER2/$CB_2$ heteromers correlates with poor patient prognosis. Also that HER2/$CB_2$ heteromers disassociate when cancer cells are treated with $\Delta^9$-tetrahydrocannabinol (THC).

Accordingly, in a first aspect the present invention provides a method of prognosis of a patient afflicted with breast cancer, comprising; determining the level of HER2/$CB_2$ heteromer expression in a biological sample obtained from said patient.

In a second aspect, the present invention provides a method of predicting the length of overall survival of a patient with breast cancer, comprising: determining the level of HER2/$CB_2$ heteromer expression in a biological sample obtained from said patient; comparing said level to standards indicative of healthy individuals or indicative of higher or lower overall survival; and thereby predicting the length of overall survival associated with said level of HER2/$CB_2$ heteromer expression In a third aspect, the present invention provides a method of predicting the length of disease-free survival of a breast cancer patient, comprising: determining the level of HER2/$CB_2$ heteromer expression in a biological sample obtained from said patient; comparing said level to standards indicative of healthy individuals or indicative of higher or lower overall survival; and thereby predicting the length of disease-free survival associated with said level of HER2/CB2 heteromer expression.

In a fourth aspect, the present invention provides a method of diagnosis or prognosis of breast cancer in a subject, the method comprising: providing a tissue of the subject; determining an expression level of HER2/$CB_2$ heteromer in the tissue; and diagnosing or prognosing breast cancer when the expression level is higher than a standard.

The step of determining an expression level of HER2/$CB_2$ heteromer in aspects 1 to 4 can be by any method known in the art. However, in some embodiments, the method of determining the expression level of HER2/$CB_2$ heteromer is co-localization protocols, co-immunoprecipitation assays, resonance energy transfer techniques, proximity ligation assays, or by the use of specific probes designed to detect the heteromers.

In a fifth aspect, the present invention provides a method of treating HER+ breast cancer comprising the step of administering a pharmaceutical agent capable of disrupting HER2/$CB_2$ heteromer thereby treating said HER+ breast cancer.

In a sixth aspect the present invention provides a kit comprising an agent capable of detecting HER2/$CB_2$ heteromer and instructions for use.

BRIEF DESCRIPTION OF THE FIGURES

The file of this patent contains at least one drawing executed in color. Copies of this patent with color drawings will be provided by the Patent and Trademark Office upon request and payment of the necessary fee FIG. 1. Representative images showing HER2, $CB_2$, and HER2-$CB_2$ heteromer expression in a HER2+ breast tumor (positive control, upper panels) and a HER2− breast tumor (negative control, lower panels). HER2 and $CB_2$ staining appear in brown, and heteromer staining in pink. Cell nuclei were stained with DAPI (blue).

DETAILED DESCRIPTION OF THE PREFERRED EMBODIMENTS OF THE INVENTION

Figure 1:
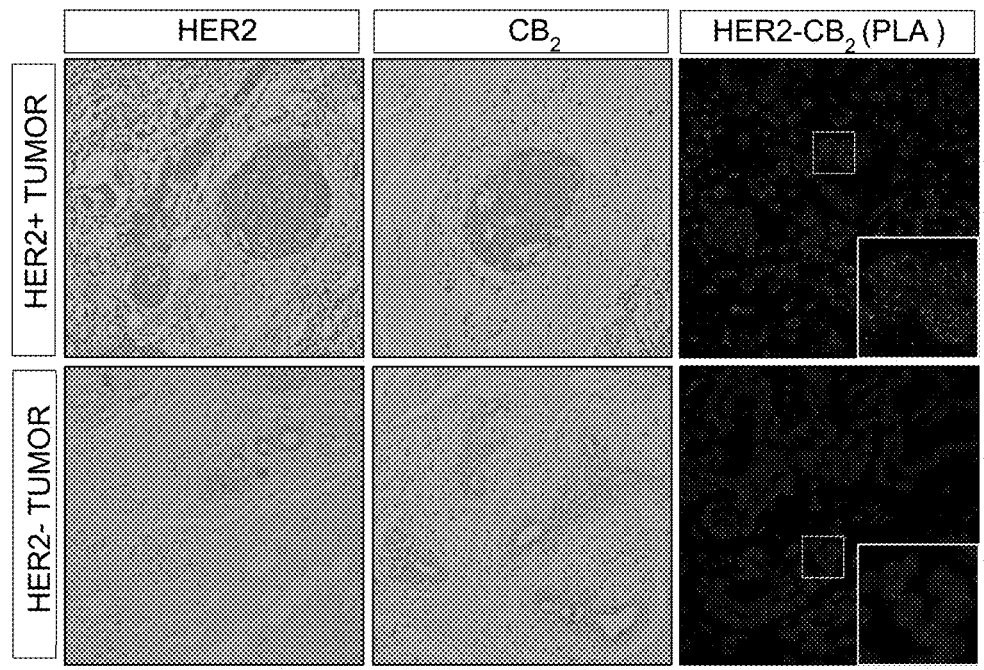

Before the present methods and kits are described, it is understood that this invention is not limited to the particular methodology, protocols, and reagents described as these may vary. It is also to be understood that the terminology used herein is for the purpose of describing particular embodiments only, and is not intended to limit the scope of the present invention which will be described by the appended claims.

It must be noted that as used herein and in the appended claims, the singular forms "a," "an," and "the" include plural reference unless the context clearly dictates otherwise. Thus, for example, reference to "a cell" includes a plurality of such cells, reference to "an antibody" includes one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the methods, devices, and materials are now described. All publications mentioned herein are incorporated herein by reference for the purpose of describing and disclosing the antibodies, proteins, nucleic acids, and methodologies which are reported in the publications which might be used in connection with the invention. Nothing herein is to be construed as an admission that the invention is not entitled to antedate such disclosure by virtue of prior invention.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

In accordance with the present invention, methods are provided for prognosis of a patient afflicted with breast cancer, especially HER2+ breast cancer, comprising determining the levels of HER2/$CB_2$ heteromer expression in a biological sample obtained from said patient.

In one embodiment, the method may comprise contacting said biological sample with a HER2/$CB_2$ heteromer binding composition.

In another embodiment, the method may further comprise comparing the levels of HER2/$CB_2$ heteromer expression in said biological sample to a standard, and thereby providing for prognosis associated with said determined levels of HER2/$CB_2$ heteromer expression.

In another embodiment, it has been found that elevated levels of HER2/$CB_2$ heteromer expression are associated with patients having a decreased length of local disease-free survival.

In one embodiment of the invention, it has been discovered that elevated levels of HER2/$CB_2$ heteromer expression is associated with patients having a decreased length of progression-free survival.

In another embodiment, it has been found that elevated levels of HER2/$CB_2$ heteromer expression are associated with patients having a decreased length of event-free survival.

The levels of HER2/$CB_2$ heteromer expression may be used as the sole factor in assessing the disease status, or along with the additional factors, including, lymph node status, estrogen receptor status, and the like.

The term "diagnosis" is used herein to refer to the identification of patient that is afflicted with breast cancer, especially HER2+ breast cancer.

"Prognosis" as used in this application means the likelihood of recovery from breast cancer or the prediction of the probable development or outcome of breast cancer, including but not limited to predicting the length of overall survival, length of breast cancer-free survival, progression-free survival, event-free survival, likelihood of reappearance of breast cancer in a patient and likelihood of breast cancer metastasis.

The phrase "overall survival" is well known to one of skill in the art and refers to the fate of the patient after diagnosis, despite the possibility that the cause of death in a patient is not directly due to the effects of the cancer. The phrase "disease-free survival" is well known to one of skill in the art and means living free of the disease being monitored. For example, if HER2/$CB_2$ heteromer expression is used to diagnose or monitor breast cancer, disease-free survival would mean free from detectable breast cancer. The phrase "likelihood of recovery" is well known to one of skill in the art and refers to the probability of disappearance of tumour or lack of tumour reappearance resulting in the recovery of the patient subsequent to diagnosis of cancer, wherein the probability is determined according to the process of the invention. The phrase "likelihood of reappearance" is well known to one of skill in the art and refers to the probability of tumour reappearance or metastasis in a patient subsequent to diagnosis of cancer, wherein the probability is determined according to the process of the invention. The phrase "event-free survival" is well known to one of skill in the art and means living without the occurrence of a particular group of defined events (for example progression of cancer) after a particular action (e.g., treatment). The phrase "Progression-free survival" is well known to one of skill in the art and refers to the length of time during and after treatment in which a patient is living with a disease that does not get worse, and can be used in a clinical study or trial to help find out how well a treatment is working. The term "metastasis" is well known to one of skill in the art and refers to the growth of a cancerous tumour in an organ or body part, which is not directly connected to the organ of the original cancerous tumour. Metastasis will be understood to include micro-metastasis, which is the presence of an undetectable amount of cancerous cells in an organ or body part which is not directly connected to the organ of the original cancerous tumour. Therefore, the present invention contemplates a method of determining the risk of further growth of one or more cancerous tumours in an organ or body part which is not directly connected to the breast.

As used herein, the phrase "biological sample" encompasses a variety of sample types obtained from a subject and useful in the procedure of the invention. Biological samples may include, but are not limited to, solid tissue samples, liquid tissue samples, biological fluids, aspirates, cells and cell fragments. Specific examples of biological samples include, but are not limited to, solid tissue samples obtained by surgical removal, a pathology specimen, an archived sample, or a biopsy specimen, tissue cultures or cells derived therefrom and the progeny thereof, and sections or smears prepared from any of these sources. Non-limiting examples are samples obtained from breast tissue, lymph nodes, and breast tumours. All or a portion of the biological sample may have a level of HER2/CB$_2$ heteromer expression characteristic of one or more disease state(s).

As used herein, a "standard" is a reference that serves as a basis for comparison of other data. A standard may include a biological sample, photographs or photomicrographs of biological samples, or normal ranges (for example, within the range of healthy individuals) derived from an analysis of biological samples. For example, standards may include normal and/or cancer tissue, cancer-free tissue or an archived pathology sample containing HER2/CB$_2$ heteromer protein expression at various levels for use as positive control, and tumour tissue or other tissue showing no HER2/CB$_2$ heteromer expression levels as negative control samples, a photograph or photomicrographs, or normal ranges derived from said samples. Such standards may be used in methods, including but not limited to, for predicting the length of disease-free and overall survival, predicting progression-free survival, predicting the risk of decreased disease-free or overall survival, predicting the likelihood of recovery of a patient suffering from cancer, predicting the likelihood of reappearance of cancer and/or metastasis in an individual having a cancer tumour, predicting the risk of reappearance of cancer, methods for screening a patient suffering from cancer to determine the risk of tumour metastasis, methods for determining the proper course of treatment for a patient suffering from cancer and methods for monitoring the effectiveness of a course of treatment for a patient suffering from cancer.

A "HER2/CB$_2$ heteromer binding composition" may include any agent, including but not limited to ligands, anti-HER2/CB$_2$ heteromer antibodies or antigen binding fragments thereof, that is capable of specifically binding to HER2/CB$_2$ heteromer. As used herein, the term "agent that binds to (or capable of binding to) HER2/CB$_2$ heteromer" refers to any molecule that specifically binds to HER2/CB$_2$ heteromer or polypeptide fragment thereof, including but not limited to, antibodies or antigen-binding fragments thereof, and thereby detects the levels of HER2/CB$_2$ heteromer expression. Such agents are preferably labelled for detection using methods well known to those of skilled in the art. Examples of labels include, but are not limited to, radiolabels, chromophores, fluorophores, enzymes, binding moieties (e.g. biotin) and the like.

"HER2", "ErbB2", "c-Erb-B2" are used interchangeably. Unless indicated otherwise, the terms "ErbB2" "c-Erb-B2" and "HER2" when used herein refer to the human protein. The human ErbB2 gene and ErbB2 protein are, for example, described in Semba et al., PNAS (USA) 82:6497-650 (1985) and Yamamoto et al. Nature 319:230-234 (1986) (Genbank accession number X03363). Examples of antibodies that specifically bind to HER2 are disclosed in U.S. Pat. Nos. 5,677,171; 5,772,997; Fendly et al., *Cancer Res.*, 50: 1550-1558 (1990); HER2 monoclonal antibody 4D5, produced by hybridoma cell line (ATCC CRL 10463), HER2 monoclonal antibody 6B3, produced by hybridoma cell line (ATCC Number PTA-5262), ErbB2 monoclonal antibody produced by hybridoma cell lines HB-11601 and HB-11602; and the like.

Antibodies or antigen-binding fragments thereof, both monoclonal and polyclonal, may be used as HER2/CB$_2$ heteromer binding composition which binds HER2/CB$_2$ heteromer protein or a polypeptide fragment thereof. Also contemplated herein as HER2/CB$_2$ heteromer binding composition any mutants of proteins which specifically bind HER2/CB$_2$ heteromer, whether by, addition (e.g., addition of a GST domain or a GFP domain), or sequence modification (e.g., site-specific mutagenesis), and the like.

The term antibody herein includes, but is not limited to, human and non-human polyclonal antibodies, human and non-human monoclonal antibodies (mAbs), chimeric antibodies, anti-idiotypic antibodies (anti-IdAb), and humanized antibodies.

The term antibody is also meant to include both intact molecules as well as fragments thereof such as, for example, Fab, F(ab).sub.2, Fab', F(ab').sub.2, Fd, Fd', Fv, and scFv, single chain antibodies (natural or recombinant) which are capable of binding to the antigen. The antibody or antigen binding component can be in solution or attached to a support (plate, beads, magnetic beads, etc.).

The antibodies or fragments of antibodies can be useful in immunofluorescence techniques employing a fluorescently labelled antibody with fluorescent microscopic, flow cytometric, or fluorometric detection. The reaction of antibodies and polypeptides of the present invention may be detected by immunoassay methods well known in the art. The antibodies of the present invention may be employed histologically as in light microscopy, imaging, immunofluorescence or immunoelectron microscopy, for in situ detection of the HER2/CB$_2$ heteromer protein in tissues samples or biopsies. In situ detection may be accomplished by removing a histological specimen from a patient and applying the appropriately labelled antibody of the present invention.

The biological sample may be treated with a solid phase support or carrier such as nitrocellulose or other solid support capable of immobilizing cells or cell particles or soluble proteins. The support may then be washed followed by treatment with the detectably labelled anti-HER2/CB$_2$ heteromer antibody. This is followed by washing of the support to remove unbound antibody. The amount of bound label on said support may then be detected by conventional means. By solid phase support is intended any support capable of binding antigen or antibodies such as, but not limited to, glass, polystyrene, polypropylene, nylon, modified cellulose, or polyacrylamide. Alternatively, the antigen may be in solution and the antibody is attached to a support (plate, beads, magnetic beads, etc.).

The binding activity of a given lot of antibody to the HER2/CB$_2$ heteromer protein may be determined according to well-known methods. Those skilled in the art will be able to determine operative and optimal assay conditions for each determination by employing routine experimentation.

In one embodiment, the invention provides methods for prognosis HER2+ breast cancer by detecting the level of expression of HER2/CB$_2$ heteromer.

A preferred embodiment of the invention provides methods for predicting the length of HER2+ breast cancer-free survival of a patient suffering from HER2+ breast cancer by determining the level of HER2/CB$_2$ heteromer expression in a biological sample obtained from said patient, comparing said level to standards indicative of healthy individuals or indicative of higher or lower length of HER2+ breast cancer-free survival, and thereby predicting the length of HER2+ breast cancer-free survival associated with said level of HER2/CB$_2$ heteromer expression, wherein elevated levels of HER2/CB$_2$ heteromer expression is associated with a decreased length of breast cancer-free survival.

In yet another embodiment of the invention, methods are provided for the determination of levels of HER2/CB$_2$ heteromer expression at an early stage of tumour development. Various stages of tumour development are well known to those of skill in the art, as exemplified in Markman, (1997), Basic Cancer Medicine, for example.

Determining Levels of HER2/CB$_2$ Heteromer Expression

Determination of HER2/CB$_2$ heteromer expression may be performed by one or more of the methods known to one of ordinary skill in the art. For example, HER2/CB$_2$ heteromer expression levels may be determined using co-localization protocols, co-immunoprecipitation assays, resonance energy transfer techniques, proximity ligation assays, or by the use of specific probes designed to detect the heteromers.

Proximity ligation assays are increasingly useful for the understanding of the biological role of molecular complexes, as well as in the study of biomarkers. For example, HER2/CB$_2$ heteromer binding compositions, i.e., compositions that specifically bind HER2/CB$_2$ heteromer can be coupled with many different detection systems to measure the presence and/or quantity of HER2/CB$_2$ heteromer. Any method known to one of skill in the art to be useful for determining an amount of HER2/CB$_2$ heteromer can be used in accordance with the present invention. Such methods include, but are not limited to, Foerster resonance energy transfer (FRET), bioluminescence resonance energy transfer (BRET), biomolecular fluorescence complementation, proximity ligation assay (PLA), and scintillation proximity assay (SPA).

Levels of HER2/CB$_2$ heteromer expression can also be detected by measuring levels of HER2/CB$_2$ heteromer protein using HER2/CB$_2$ heteromer binding compositions. The detection of HER2/CB$_2$ heteromer protein levels may be carried out using any of the methods known to one of ordinary skill in the art including, but not limited to, chemiluminescence methods, histochemical staining or biochemical detection (i.e., immuno-histochemistry assays), Western Blot analysis, flow cytometry, immuno-precipitation (or the equivalent thereof for non-antibody agents), Plasmon resonance absorbance measurement, and the like. In one embodiment of the invention, the method of detecting HER2/CB$_2$ heteromer protein levels is an immunoassay (such as an ELISA), which includes the use of at least one antibody. In yet another embodiment of the invention, HER2/CB$_2$ heteromer staining, in tissue sample for example, formalin-fixed, paraffin-embedded tissue sections can be carried out by immuno-histochemistry using an anti-HER2/CB$_2$ heteromer antibody, and determining the expression of HER2/CB$_2$ heteromer.

Classification of Patients

The term "breast cancer" as used herein, includes ductal carcinoma in situ (intraductal carcinoma), lobular carcinoma in situ, invasive (or infiltrating) ductal carcinoma, invasive (or infiltrating) lobular carcinoma, inflammatory breast cancer, triple-negative breast cancer, paget disease of the nipple, phyllodes tumor, angio-sarcoma or invasive breast carcinoma. In some embodiments, the invasive breast carcinoma is further categorized into subtypes. In some embodiments, the subtypes include adenoid cystic (or adenocystic) carcinoma, low-grade adenosquamous carcinoma, medullary carcinoma, mucinous (or colloid) carcinoma, papillary carcinoma, tubular carcinoma, metaplastic carcinoma, micropapillary carcinoma or mixed carcinoma. Preferably the term as used herein refers to HER2+ breast cancer.

The term "patient afflicted with breast cancer" means that a human subject has been diagnosed as having breast cancer as defined herein.

The patients can be classified by comparing the levels of HER2/CB$_2$ heteromer expression in the biological sample obtained from a patient to a standard. For example, after measuring the HER2/CB$_2$ heteromer expression level in the sample, the measured level is compared to a standard. This standard is a level of expression of HER2/CB$_2$ heteromer used to evaluate the level of expression of HER2/CB$_2$ heteromer in the biological sample of a patient. For example, in one embodiment, when the levels of HER2/CB$_2$ heteromer expression in the patient sample are higher than that of the standard, the patient sample will be considered to have elevated levels of HER2/CB$_2$ heteromer expression. Conversely, in another embodiment, when the levels of HER2/CB$_2$ heteromer expression in the sample are lower than the standard, the sample will be considered to have low levels of HER2/CB$_2$ heteromer expression.

In another embodiment, patients can be assigned a "score" associated with the HER2/CB$_2$ heteromer expression in a given biological sample. A sample may be "scored" during the diagnosis or monitoring of breast cancer. Scoring may be determined by the levels of expression of HER2/CB$_2$ heteromer in a biological sample. In one embodiment, elevated levels of HER2/CB$_2$ heteromer expression in a biological sample are given a higher score as compared to low levels of HER2/CB$_2$ heteromer expression, which is given a comparatively lower score. Scoring may also be determined by visual examination of samples by immunohistochemistry. In another embodiment, more quantitative scoring involves determining the two or more parameters, for example (i) intensity of staining and (ii) the proportion of stained ("positive") cells that are sampled. Based on these multiple parameters scores may be assigned that reflect increasing levels of positive staining.

Thus, in one embodiment, a score associated with the levels of HER2/CB$_2$ heteromer expression in a biological sample obtained from a patient can be compared to the score associated with the levels of HER2/CB$_2$ heteromer expression in the standard or to cells having no, low or elevated levels of HER2/CB$_2$ heteromer expression used as controls. Such comparison may provide a basis for better prognosis of the patient. For example, in one embodiment, methods of the invention may score the levels of HER2/CB$_2$ heteromer expression by using a scale of 0 to 3+, where 0 is negative (no detectable HER2/CB$_2$ heteromer expression), 1+ and 2+ are associated with a weak and weak to moderate staining, respectively, and 3+ is associated with high intensity staining, in more than 10% of tumour cells; and wherein a lower score indicates a better prognosis of patients.

Prognosis of patients expressing various levels of HER2/CB$_2$ heteromer can be carried out using single variable or multi-variable analysis. These methods determine the likelihood of a correlation between one or more variables and a given outcome. In one embodiment, the methods will determine the likelihood of a correlation between HER2/CB$_2$ heteromer expression levels (or HER2/CB$_2$ heteromer expression levels coupled with another variable) and disease-free or overall survival of breast cancer patients. Any one of a plurality of methods well known to those of ordinary skill in the art for carrying out these analyses may be used. An example of single variable analysis is the Kaplan-Meier method or the log-rank test. An example of multi-variable analysis is the Cox proportional-hazards regression model. The methods of the invention may further comprise analyzing the levels of HER2/CB$_2$ heteromer expression in conjunction with additional breast cancer markers. Cox proportional ratio provides a hazard ratio or a risk for disease-free and overall survival for patient with varying level of HER2/CB$_2$ heteromer expression.

Survival analysis using methods of Kaplan and Meier is the recommended statistical technique for use in cancer trials. It is applied by analyzing the distribution of patient survival times following their recruitment to a study. The analysis expresses these in terms of the proportion of patients still alive up to a given time following recruitment. In graphical terms, a plot of the proportion of patients surviving against time has a characteristic decline (often exponential), the steepness of the curve indicating the efficacy of the treatment being investigated. The more shallow the survival curve, the more effective the treatment. Kaplan-Meier analysis can be used to test the statistical significance of differences between the survival curves associated with two different treatments.

In one embodiment, after the levels of expression of HER2/CB$_2$ heteromer in the sample obtained from a patient have been determined and compared to the standard, the patient is then classified into a group having a certain likelihood of disease-free or overall survival. Then the likelihood of disease-free or overall survival for the patient is assessed based on the likelihood of disease-free or overall survival for patients in that group. For example, the biological sample obtained from a patient may be determined to have elevated levels of HER2/CB$_2$ heteromer expression relative to the standard. This patient would then be classified into a group of patients having elevated levels of HER2/CB$_2$ heteromer expression. Since, in accordance with the present invention, it has been discovered that there is a decreased length of disease-free or overall survival for the group of patients expressing elevated levels of HER2/CB$_2$ heteromer, the specific patient afflicted with cancer would be considered to have a decreased length of disease-free or overall survival.

Kits

The present detection method is desirably carried out in any conventional test kit format. For example, the immunoassay can be a solid capture, competitive, or sandwich immunoassay.

The solid phase capture immunoassay test kit includes an antibody capable of binding to HER2/CB$_2$ heteromer and having a label to permit detection, and a solid support. The solid support can either be sold as part of the test kit or separate from it. When utilized in the detection method of the present invention, the antibody is contacted with the test sample. The resulting mixture is contacted with the solid support so that the complex binds to the support. After removal of unbound material the antibody can then be detected.

In a particularly preferred form of the present invention, the mixture of HER2/CB$_2$ heteromer antibody and test sample can be contacted with an affinity matrix so that the complex binds to the affinity matrix. After removal of unbound material, the complex is eluted from the affinity matrix and allowed to contact and adsorb to the solid support. The affinity matrix can also be used to bind to the complex and thereby separate the complex from the remainder of the test sample-HER2/CB$_2$ heteromer antibody mixture in the sandwich and competitive formats. In each, the complex can be subsequently eluted from the affinity matrix and into absorptive contact with the solid support.

The solid support used in any of the immunoassay test kit formats may be any water insoluble, water suspensible solid material conventionally utilized in such kits. Suitable examples are polymeric membranes, plastic or glass beads, test tubes, or microtiter plates. The binding substance in the complex may be bound to the solid carrier by covalent binding or adsorption. When test tubes or microtiter plates are utilized, such bonding takes place at the inner walls of these carriers.

In competitive and sandwich immunoassay test kits, the kit can be merchandised with the binding substance already bound to the solid support. Such application to the solid support surface is achieved by contacting the binding substance with the solid support and maintaining such contact for sufficient time to permit the first region of the binding substance to bond to the solid support. Typically, such contact takes one to eighteen hours, preferably four hours. The non-adhered binding substance is then separated from the insolubilized binding substance (i.e., that which is bound to the solid support) and the solid support is then washed.

In all three immunoassay test kit formats, the test sample and the HER2/CB$_2$ heteromer antibody are placed in contact with each other and allowed to incubate for sufficient time to permit binding. Typically, such binding takes two hours. Such contact desirably is followed by contacting the test sample and HER2/CB$_2$ heteromer antibody mixture with a solid support. For the solid phase capture assay, the complex binds directly to the solid support, while the complex binds indirectly (i.e., through the binding substance) to the solid support in the competitive assay or sandwich immunoassays. For all three immunoassay test kit formats of the present invention, after allowing sufficient time for incubation, residual test sample and HER2/CB$_2$ heteromer antibody mixture is separated from the insolublized material bound to the solid support. The insoluble material is then washed.

It is to be understood that application of the teachings of the present invention to a specific problem or environment will be within the capability of one having ordinary skill in the art in light of the teachings contained herein. The present invention is more fully illustrated by the following non-limiting examples.

Example 1: HER2/CB$_2$ Heteromer Expression as a Prognostic Tool in HER2+ Breast Cancer The expression of HER2-CB$_2$ heteromers was analyzed in a tissue microarray (TMA) containing 57 HER2+ breast cancer samples corresponding to cases operated at 12 de Octubre Hospital (Madrid, Spain) between 1999 and 2013. The expression analysis was performed by Proximity Ligation Assay, using the Duolink II in situ PLA detection kit (Olink, Bioscience, Uppsala, Sweden). The samples were observed under a confocal microscope, and the red fluorescent signals (corresponding to the heteromers) were processed with ImageJ software. Samples were ranked by HER2-CB$_2$ heteromer expression, and the best cutoff was manually selected.

Figure 2:
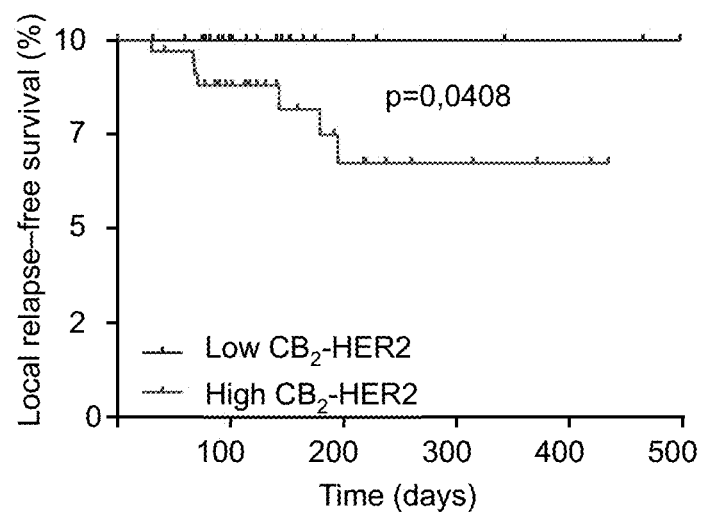
FIG. 2. Kaplan-Meier curves for local relapse-free survival. Samples were ranked by HER2-$CB_2$ heteromer expression and distributed in two groups (low and high expression) by selecting the best cutoff manually.

First, we performed the staining controls for HER2, CB$_2$ and HER2-CB$_2$ heteromers (see FIG. 1). Second, we ranked samples by PLA signal (number of pink dots/PLA-positive cells), and analyzed potential associations with clinical parameters related to patient prognosis. As shown in FIG. 2 we found a significant correlation between high heteromer expression and lower local relapse-free survival.

Example 2: Mechanism of Action of THC

We previously reported that THC, when used at concentrations that produce anti-tumor responses, disrupts HER2-$CB_2$ heteromers in BT474 cells. As discussed in Example 1, we observed these effects using Proximity Ligation assays (PLAs) and Bioluminescence Resonance Energy Transfer (BRET) assays. We also observed a concomitant degradation of HER2 in the same cell line, which suggests that THC induces its anti-proliferative effects by disrupting the HER2-$CB_2$ heteromers and destabilizing HER2.

Figure 3:
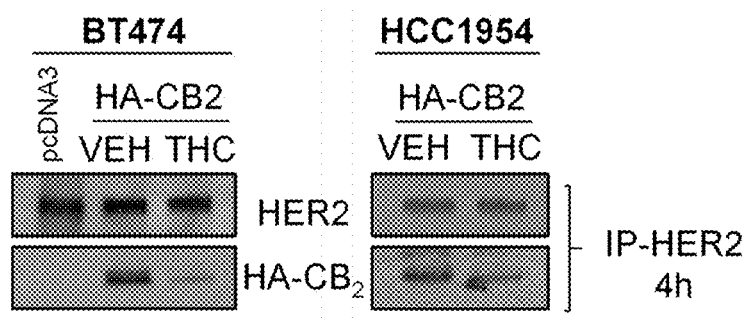
FIG. 3. Western blot analysis of HER2 and $CB_2$ in the indicated cell lines. Cells were transfected with a $CB_2$-HA encoding plasmid and treated with THC for 4 h. HER2 was then immune-precipitated with an anti-HER2 antibody, and blots were developed with anti-HA antibodies.

We have confirmed that THC disrupts HER2-$CB_2$ heteromers by a different technique (co-immuno-precipitation, co-IP), in two different HER2+ breast cancer cell lines (BT474 and HCC1954). Results are shown in FIG. 3.

Figure 4:
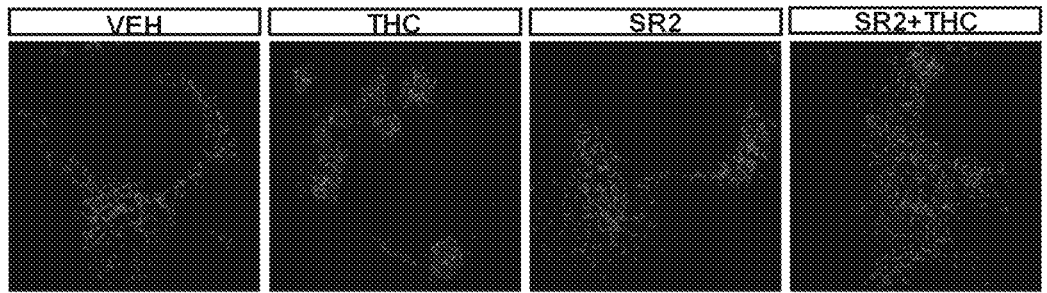
FIG. 4. HER2-$CB_2$ heteromer expression in HCC1954 cells. Representative images of the PLA experiments, in response to the indicated treatments.

We have also undertaken PLAs in HCC1954 cells that show that SR2 (a selective $CB_2$ antagonist) blocks THC-induced heteromer disruption. These observations confirm that THC breaks the heteromers by acting on $CB_2$ (FIG. 4).

Figure 5:
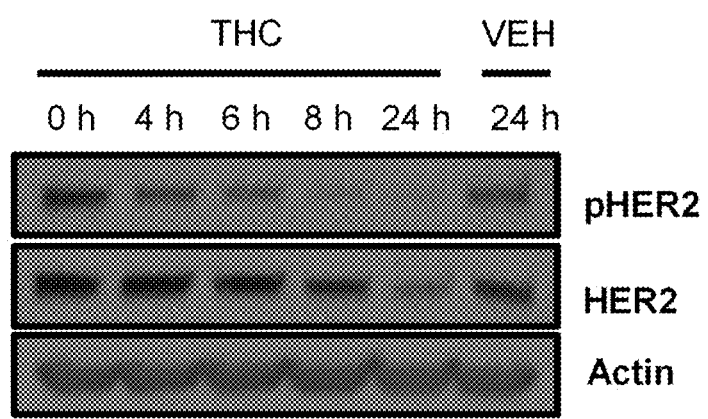
FIG. 5. Protein expression in HCC1954 cells. Protein expression analysis by Western blot of total and phosphorylated (i.e., activated) HER2 in response to THC.

We previously observed degradation of HER2 upon THC treatment in BT474 cells. We have now confirmed this observation by Western blot in HCC1954 cells (FIG. 5).

Figure 6:
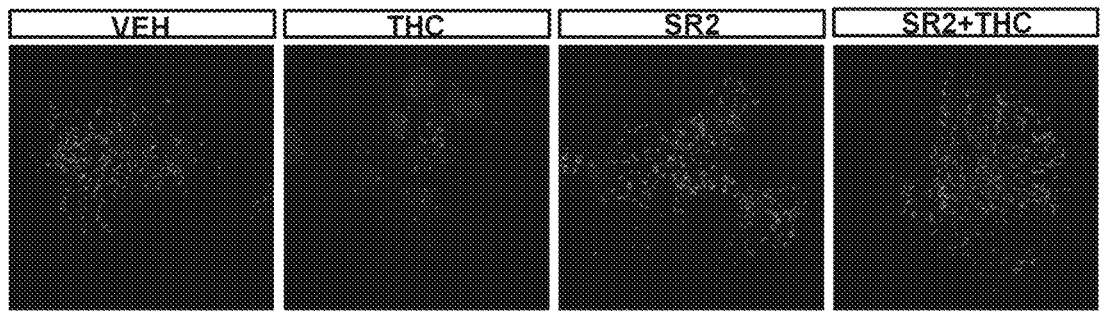
FIG. 6. HER2-HER2 dimer expression in HCC1954 cells. Representative images of the PLA experiments, in response to the indicated treatments.

We have conducted PLAs that show that THC disrupts not only HER2-$CB_2$ but also HER2-HER2 dimers (which are very well known signaling complexes that drive tumor progression in HER2+ breast cancer). These data are shown in FIG. 6.

Methods and Materials
Cells, Cell Cultures, and Transfections

BT474 and HCC1954 human breast adenocarcinoma cells were maintained in RPMI medium supplemented with 10% FBS, and penicillin/streptomycin.

In Situ Proximity Ligation Assays (PLA)

Cells were grown on glass coverslips and fixed in 4% paraformaldehyde, washed with PBS containing 20 mM glycine, permeabilized with the same buffer containing 0.05% Triton® X-100, and washed successively with PBS. HER2-$CB_2$R heteromers were detected using the Duolink in situ Probemarker kit (Olink, Bioscience, Uppsala, Sweden). After 1 h of incubation at 37° C. with the blocking solution in a preheated humidity chamber, cells were incubated overnight in the antibody dilution medium with a mixture of equal amounts of rabbit anti-$CB_2$ antibody (1:50, Cayman Chemical, Ann Arbor, Mich.) directly linked to a plus PLA probe, and rabbit anti-HER2 antibody (1:50, Santa Cruz Biotechnology, Santa Cruz, Calif., US) directly linked to a minus PLA probe. Cells were washed with wash buffer A at room temperature and incubated in a preheated humidity chamber for 30 min at 37° C. with the ligation solution (Duolink® II ligation stock, 1:5, and Duolink II ligase, 1:40) to induce annealing and ligation of the two DNA probes. Amplification was done with the Duolink II detection reagents red kit, which contains fluorescence nucleotides. After exhaustive washing at room temperature with wash buffer B, cells were mounted using mounting medium with DAPI. The samples were observed under a Leica SP2 confocal microscope (Leica Microsystems, Mannheim, Germany). Red fluorescent images were processed with ImageJ software. PLA requires that both receptors be close enough to allow the two different antibody-DNA probes to be able to ligate (<17 nm) ((Soderberg et al., (2008), Methods., 45: 227-232; Trifilieff et al., (2011), BioTechniques, 51: 111-118). If the receptors are within sufficient proximity, a punctate fluorescent signal can be detected by confocal microscopy.

Western Blotting

HCC1954 cells were treated with RIPA buffer (50 mM Tris, 150 mM NaCl, 1% NP-40, 0.5% sodium deoxycholate, and 0.1% sodium dodecyl sulfate), containing a cocktail of protease inhibitors (pepstatin, leupeptin, aprotinin, quimostatin, antipain, and phenylmethylsulfonyl fluoride) and phosphatase inhibitors ($Na_3VO_4$ and NaF; Sigma Chemical Co., St. Louis, Mo.). Proteins separated by sodium dodecyl sulfate-10% polyacrylamide reducing gels were transferred to polyvinylidene difluoride membranes (Bio-Rad Laboratories, Hercules, Calif.). After blocking with 5% skim milk and 1% bovine serum albumin, membranes were incubated with the anti-ErbB2 antiserum (Santa Cruz Biotechnology, Santa Cruz, Calif.) diluted 1:500 for 3 h at room temperature. Bound antibodies were revealed with a goat anti-rabbit immunoglobulin G (IgG) peroxidase-labeled antibody (Zymed Laboratories, South San Francisco, Calif.). A chemiluminescence detection system (Amersham Pharmacia Biotech, Piscataway, N.J.) was used to reveal peroxidase. Controls were carried out with an anti-actin monoclonal antibody (MAb; Boehringer Mannheim, Indianapolis, Ind.) diluted 1:5,000 followed by an anti-mouse IgG peroxidase-labeled antibody diluted 1:4,000 (Zymed).

Co-Immunoprecipitation Assays

HCC1954 and BT474 cells were transiently transfected with pcDNA3-HA-h$CB_2$ or the corresponding empty vector (pcDNA3), using Fugene HD Transfection Reagent (Promega, Madison, Wis.). 48 h after transfection, cells were treated with 3 μM THC or the corresponding vehicle (DMSO) for 4 h, and lysed using a specific buffer for co-immunoprecipitation (40 mM Hepes pH 7.5, 120 mM NaCl, 1 mM EDTA, 10 mM sodium pyrophosphate, 10 mM sodium glycerophosphate, 50 mM sodium fluoride, 0.5 mM sodium orthovanadate, 0.3% CHAPS and supplemented with 1 mM benzamidine and 0.1 mM PMSF in fresh). Cell lysates (1 mg) were immunoprecipitated using 5 μg of anti-ErbB2 antibody (Neu C-18, Santa Cruz Biotechnology, Santa Cruz, Calif., US) covalently coupled to 5 μL protein G-sepharose. After immunoprecipitation, proteins were separated by SDS-10% polyacrylamide reducing gels and transferred to PVDF membranes. After blocking with 5% w/v non-fat dry milk in TBST, membranes were incubated with anti-ErbB2 antibody (1:1000) and anti-HA antibody (1:1000, Cell Signaling Technology, Danvers, Mass.) overnight at 4° C. Bound antibodies were detected with a donkey anti-rabbit immunoglobulin G (IgG) peroxidase-labeled antibody (GE Healthcare, UK). A chemiluminescence detection system (Bio-Rad, California, EEUU) was used to detect the peroxidase activity.

What is claimed is:

1. A method comprising:
   providing a test sample comprising a biological sample from a subject;
   contacting the test sample with a HER2/$CB_2$ heteromer binding composition comprising one or more antibodies that specifically bind to a HER2/$CB_2$ heteromer, wherein the one or more antibodies comprise anti-HER2 antibodies, anti-$CB_2$ antibodies, or both, or one or more antigen-binding fragments of the one or more antibodies to form a mixture;
   incubating the mixture for a time sufficient to permit binding;
   determining from the mixture a level of HER2/$CB_2$ heteromer in the biological sample;

comparing the level of HER2/CB$_2$ heteromer in the biological sample to a standard level of HER2/CB$_2$ heteromer obtained from normal or cancer-free tissue or from an archived pathology sample containing a known level of HER2/CB$_2$ heteromer protein expression;

classifying the level of HER2/CB$_2$ heteromer in the biological sample as not detectable, low, or elevated based on the comparison; and treating the subject classified as having an elevated level of HER2/CB$_2$ heteromer by administering a pharmaceutical agent capable of disrupting a HER2/CB$_2$ heteromer, wherein the pharmaceutical agent capable of disrupting the HER2/CB$_2$ heteromer is $\Delta^9$-tetrahydrocannabinol.

2. The method of claim 1, wherein the one or more antibodies comprise a non-human monoclonal antibody, a chimeric antibody, or a humanized antibody.

3. The method of claim 1, wherein determining a level of HER2/CB$_2$ heteromer in the biological sample comprises a co-localization assay, a co-immunoprecipitation assay, a resonance energy transfer technique, and a proximity ligation assay.

4. The method of claim 1, wherein determining a level of HER2/CB$_2$ heteromer in the biological sample comprises a proximity ligation assay (PLA).

5. The method of claim 1, wherein determining a level of HER2/CB$_2$ heteromer in the biological sample comprises a chemiluminescence method, a histochemical staining method, or a biochemical detection method.

6. The method of claim 5, wherein the biochemical detection method comprises an immuno-histochemistry assay, a Western Blot analysis method, a flow cytometry-based method, or an immuno-precipitation method.

7. The method of claim 1, wherein the biological sample comprises a solid tissue sample, a blood sample, a biological fluid, an aspirate, a cell, or a cell fragment.

8. The method of claim 1, wherein the biological sample comprises a surgically removed tissue sample, a pathology specimen, an archived sample, or a biopsy specimen.

9. The method of claim 1, wherein the biological sample comprises a breast tissue sample, a lymph node sample, or a breast tumor sample.

10. The method of claim 1, wherein the standard level is obtained from an archived pathology sample containing a known level of HER2/CB$_2$ heteromer protein expression.

11. The method of claim 1, wherein the standard level is obtained from a normal or cancer-free tissue sample.

* * * * *

UNITED STATES PATENT AND TRADEMARK OFFICE
CERTIFICATE OF CORRECTION

| | | |
|---|---|---|
| PATENT NO. | : 10,753,935 B2 | Page 1 of 1 |
| APPLICATION NO. | : 16/028704 | |
| DATED | : August 25, 2020 | |
| INVENTOR(S) | : Cristina Sánchez Garcia, Sandra Blasco Benito and Eduardo Pérez Gómez | |

It is certified that error appears in the above-identified patent and that said Letters Patent is hereby corrected as shown below:

On the Title Page (63), Column 1, Line 2, Delete "PCT/AU2017/051145" and insert -- PCT/AU2017/051146 --.

(56), Column 2, "Other Publications" at Line 3, Delete "Encocannabinoid" and insert
-- Endocannabinoid --.

(56), Column 2, "Other Publications" at Line 7, Delete "Universtiy" and insert -- University --.

Signed and Sealed this
Fifteenth Day of December, 2020

Andrei Iancu
*Director of the United States Patent and Trademark Office*